(12) United States Patent
Duff et al.

(10) Patent No.: US 6,269,811 B1
(45) Date of Patent: Aug. 7, 2001

(54) PRESSURE SUPPORT SYSTEM WITH A PRIMARY AND A SECONDARY GAS FLOW AND A METHOD OF USING SAME

(75) Inventors: Winslow K. Duff, Export; Patrick W. Truitt, Pittsburgh; Douglas W. Keeports, Murrysville, all of PA (US)

(73) Assignee: Respironics, Inc., Pittsburgh, PA (US)

( * ) Notice: Subject to any disclaimer, the term of this patent is extended or adjusted under 35 U.S.C. 154(b) by 0 days.

(21) Appl. No.: 09/405,565

(22) Filed: Sep. 24, 1999

Related U.S. Application Data

(60) Provisional application No. 60/108,354, filed on Nov. 13, 1998.

(51) Int. Cl.$^7$ .................................................. A61M 16/00
(52) U.S. Cl. ................................ 128/204.21; 128/204.18
(58) Field of Search ..................... 128/204.21, 204.23, 128/204.26, 203.12, 204.18

(56) References Cited

U.S. PATENT DOCUMENTS

| | | |
|---|---|---|
| Re. 17,512 | 12/1929 | McKeeson . |
| 3,276,462 | 10/1966 | Matchett . |
| 3,357,428 | 12/1967 | Carlson . |
| 3,503,393 | 3/1970 | Manley . |
| 3,595,228 | 7/1971 | Simon et al. ................... 128/202.22 |
| 3,693,653 | 9/1972 | Cramer et al. . |
| 3,722,510 * | 3/1973 | Parker ............................ 128/205.12 |
| 4,141,354 | 2/1979 | Ismach . |
| 4,141,356 | 2/1979 | Smargiassi . |
| 4,148,311 | 4/1979 | London et al. . |
| 4,155,357 | 5/1979 | Dahl ............................... 128/102.22 |
| 4,345,593 | 8/1982 | Sullivan ......................... 128/204.26 |
| 4,364,384 | 12/1982 | Warncke et al. ............... 128/204.28 |
| 4,381,002 | 4/1983 | Mon ............................... 128/204.24 |
| 4,414,982 | 11/1983 | Durkan ............................... 600/529 |
| 4,433,685 | 2/1984 | Giorgini et al. ............... 128/204.26 |
| 4,554,916 | 11/1985 | Watt ............................... 128/203.12 |
| 4,705,034 | 11/1987 | Perkins .......................... 128/204.21 |
| 4,766,894 | 8/1988 | Legrand et al. ............... 128/204.21 |
| 4,825,802 | 5/1989 | Le Bec ........................... 128/202.22 |
| 4,838,259 | 6/1989 | Gluck et al. ................... 128/201.21 |
| 4,873,971 | 10/1989 | Perkins .......................... 128/204.28 |
| 4,932,401 * | 6/1990 | Parkins .......................... 128/203.12 |
| 4,932,402 | 6/1990 | Snook et al. ................... 128/204.23 |
| 4,989,597 * | 2/1991 | Werner ........................... 128/203.12 |
| 5,038,770 | 8/1991 | Perkins .......................... 128/204.18 |
| 5,159,924 * | 11/1992 | Cegielski et al. .............. 128/203.12 |
| 5,265,594 | 11/1993 | Olsson et al. .................. 128/204.18 |
| 5,315,989 | 5/1994 | Tobia .............................. 128/204.28 |
| 5,320,092 | 6/1994 | Ryder ............................. 128/202.22 |
| 5,390,666 | 2/1995 | Kimm et al. ................... 128/204.26 |
| 5,494,028 | 2/1996 | Devries et al. ................ 128/205.24 |
| 5,495,848 | 3/1996 | Aylsworth et al. ............ 128/207.18 |
| 5,522,381 * | 6/1996 | Olsson et al. .................. 128/203.12 |
| 5,531,218 * | 7/1996 | Krebs ............................. 128/203.12 |
| 5,558,083 * | 9/1996 | Bathe et al. .................... 128/203.12 |
| 5,558,086 | 9/1996 | Smith et al. ................... 128/204.26 |
| 5,592,934 * | 1/1997 | Thwaites ........................ 128/203.12 |
| 5,603,315 | 2/1997 | Sasso, Jr. ....................... 128/204.18 |
| 5,649,531 * | 7/1997 | Heinonen ....................... 128/203.12 |
| 5,651,358 * | 7/1997 | Briend et al. .................. 128/203.12 |
| 5,660,171 | 8/1997 | Kimm et al. ................... 128/204.23 |

OTHER PUBLICATIONS

Oxygen Conserver Advertisement, Respiratory Therapy Products, Fall 1997.

* cited by examiner

*Primary Examiner*—Aaron J. Lewis
(74) *Attorney, Agent, or Firm*—Michael W. Haas

(57) ABSTRACT

A pressure support system that includes a pressure generating system employing a pressure generator that provides a primary flow of gas to a patient and a supplemental gas system providing a supplemental flow of gas to the patient. A selectively acutable valve associated with the supplemental gas system controls the supplemental flow of gas to the patient, and a control unit coupled to the pressure generating systems controls the valve based on conditions of the pressure generator in the pressure generating system, thereby controlling the flow of the supplemental gas to the patient based on the detected conditions of the pressure generator.

24 Claims, 2 Drawing Sheets

PRESSURE SUPPORT SYSTEM WITH A PRIMARY AND A SECONDARY GAS FLOW AND A METHOD OF USING SAME

CROSS REFERENCE TO RELATED APPLICATION

This application claims priority under 35 U.S.C. § 119(e) from U.S. Provisional Patent Application No. 60/108,354 filed Nov. 13, 1998.

BACKGROUND OF THE INVENTION

1. Field of the Invention

The present invention pertains to a pressure support system for providing a primary flow of gas and a supplemental flow of gas to a patient, and, in particular, to such a system wherein the primary flow of gas is provided by a pressure generator and wherein the supplemental flow of gas to the patient is controlled based on the operating conditions of the pressure generator.

2. Description of the Related Art

It is known to provide a gas flow to a patient using a pressure support system to treat a medical disorder. For example, is it known to use a continuous positive airway pressure (CPAP) device, which is a single-limb pressure support system having a passive exhaust, to supply a constant positive pressure to the patient to treat obstructive sleep apnea (OSA). It is also known to provide a positive pressure that varies with the patient's breathing cycle, patient's effort or based on the condition of the patient, such as whether the patient is experiencing or likely to experience snoring, an apnea, or hypopnea.

Such devices typically include a pressure generator, such as a blower or piston with a pressure regulator or pressure regulating capability, the pressure support device is a variable pressure device, that creates a flow of breathing gas having an elevated pressure. A single conduit, typically a flexible tube, is coupled to the pressure generator to carry the breathing gas to the patient. A patient interface, such as a nasal and/or oral mask, nasal cannula, trachea tube, intubation tube or full face mask, couples the gas flow from the conduit to the patient's airway. The conduit and/or patient interface generally includes a vent for exhausting exhaled gas to atmosphere. The vent is considered a passive exhaust system because there are no selectively actuatable valves that control the flow of exhaust gas associated with the vent.

It is also common to provide a control system to control the flow of pressurized gas to the patient. The control system ranges from the relatively simple, controlling the pressure generator based on inputs from the patient or from a few monitored parameters, to the relatively complex, controlling the pressure generator in a feedback fashion based on monitored conditions of the patient, such as the patient's respiration. In many applications, these devices are used in the home and positioned at the patient's bedside to provide the positive pressure therapy to the patient throughout the night while the patient sleeps wearing the patient interface device.

In many instances, it is also desirable to provide the patient with a supplemental gas, such as oxygen or an oxygen mixture, in addition to the primary flow of gas, which is typically air, provided by the pressure generating system. It is conventional to introduce the supplemental flow of gas into the conduit or at the patient interface device, both of which are downstream of the pressure generator in the pressure generating system.

When introducing a flammable gas or a gas, such as oxygen, which readily promotes combustion, into the pressure support system, safety concerns dictate that steps be taken to minimize the risk of fire. For example, if the pressure generator should fail or be shut off while the supplemental gas, such as oxygen, remains on, there is a chance that the supplemental gas will continue to fill the conduit and/or patient interface and backup into the pressure generator. Typically, pressure generators are designed with this eventuality in mind and are optimized for safety against fire even if oxygen backs up into the device through the conduit, for example, by using electrical circuits that will not produce a spark or reach temperatures exceeding 300° C. during single fault failures. It is also known to provide gas-tight internal airways in the pressure generator so that the supplemental gas can not enter the enclosure in which the pressure generator and its associated electronics are housed. Furthermore, it is also known to provide a check valve in the conduit (breathing circuit) between the pressure generator and the introduction point for the supplemental gas. This valve prevents gas from backing up into the pressure generator if the pressure generator ceases functioning by exhausting the gas in the breathing circuit to atmosphere.

It can be appreciated, however, that creating electrical circuits that will not produce a spark or reach temperatures exceeding 300° C. during single fault failures or creating gas-tight units increase the cost of the entire pressure support device. This is exacerbated by the fact that generally less than half of the pressure support systems on the market are used in conjunction with a supplemental supply of oxygen. Providing a check valve in the breathing circuit between the pressure generator and the introduction point for the supplemental gas, while effective in blocking the backup of the supplemental gas into the pressure generating device, does not prevent a buildup of such gas in the room where the device is located should the above-described scenario occur. This latter point is also true for the first two conventional safety precautions discussed above. The buildup of supplemental gas, such as oxygen, in a room is particularly disadvantageous because of the risk of sparks from other ignition sources, such as electronic equipment, e.g., televisions, telephones, radios, etc, pilot lights and electric or gas heaters.

SUMMARY OF THE INVENTION

Accordingly, it is an object of the present invention to provide a pressure support system that can be used in conjunction with a supplemental gas, such as oxygen, to deliver the supplemental gas to that patient and that does not suffer from the disadvantages of conventional systems discussed above. This object is achieved, according to one embodiment of the present invention, by providing a pressure support system that includes a pressure generating system having a pressure generator that provides a primary flow of gas to a patient and a supplemental gas system adapted to provide a supplemental flow of gas to the patient. The pressure support system also includes a selectively acuatable valve associated with the supplemental gas system and a control unit. The valve regulates the supplemental flow of gas to the patient provided by the supplemental gas system. The control unit is coupled to the pressure generating system and the valve, and controls actuation of the valve based on the conditions of the pressure generator in the pressure generating system, so that if, for example, the pressure generator fails or is shut off, the control unit causes the valve to close, thereby shutting off the supplemental gas flow.

It is a further object to provide the user of the above-described pressure support system the additional ability to easily and readily determine whether the supplemental flow of gas is being delivered. This object is achieved by providing a monitoring system coupled to the above-described supplemental gas system. The monitoring system monitors the supplemental flow of gas in and provides an output indicative of whether gas is flowing in the supplemental gas system.

It is another object of the present invention to operate the above-described pressure support system of the present invention so as to conserve the supplemental gas being delivered to the patient as the supplemental gas flow. This object is achieved by monitoring the respiratory cycle of the patient and causing the supplemental gas system to deliver the supplemental flow of gas to the patient only during a selected portion of the respiratory cycle, as opposed to the entire respiratory cycle. This is accomplished by causing the valve to open at an appropriate time to deliver the supplemental gas during the selected portion of a respiratory cycle, such as during inspiration, and closing the valve at all other times during the respiratory cycle.

It is a still further object of the present invention to operate the above-described pressure support system to control the dosage of supplement gas delivered to the patient when the supplemental gas system is actuated. This object is achieved by causing the valve to open according to a predetermined duty ratio, thereby controlling an amount of supplemental gas delivered to a patient during the portion of a respiratory cycle in which the valve is operating.

It is yet another object of the present invention to provide a method of providing pressure support to a patient in conjunction with providing a supplemental gas, such as oxygen, to that patient and that does not suffer from the disadvantages of conventional techniques discussed above. This object is achieved, according to one embodiment of the present invention, by providing a primary flow of gas to the patient via a pressure generator in a first flow system, providing a supplemental flow of gas to the patient via a second flow system, monitoring a condition of the pressure generator in the first flow system, and controlling the supplemental flow of gas based on the monitored condition of the pressure generator.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EXEMPLARY EMBODIMENTS OF THE PRESENT INVENTION

Figure 1:
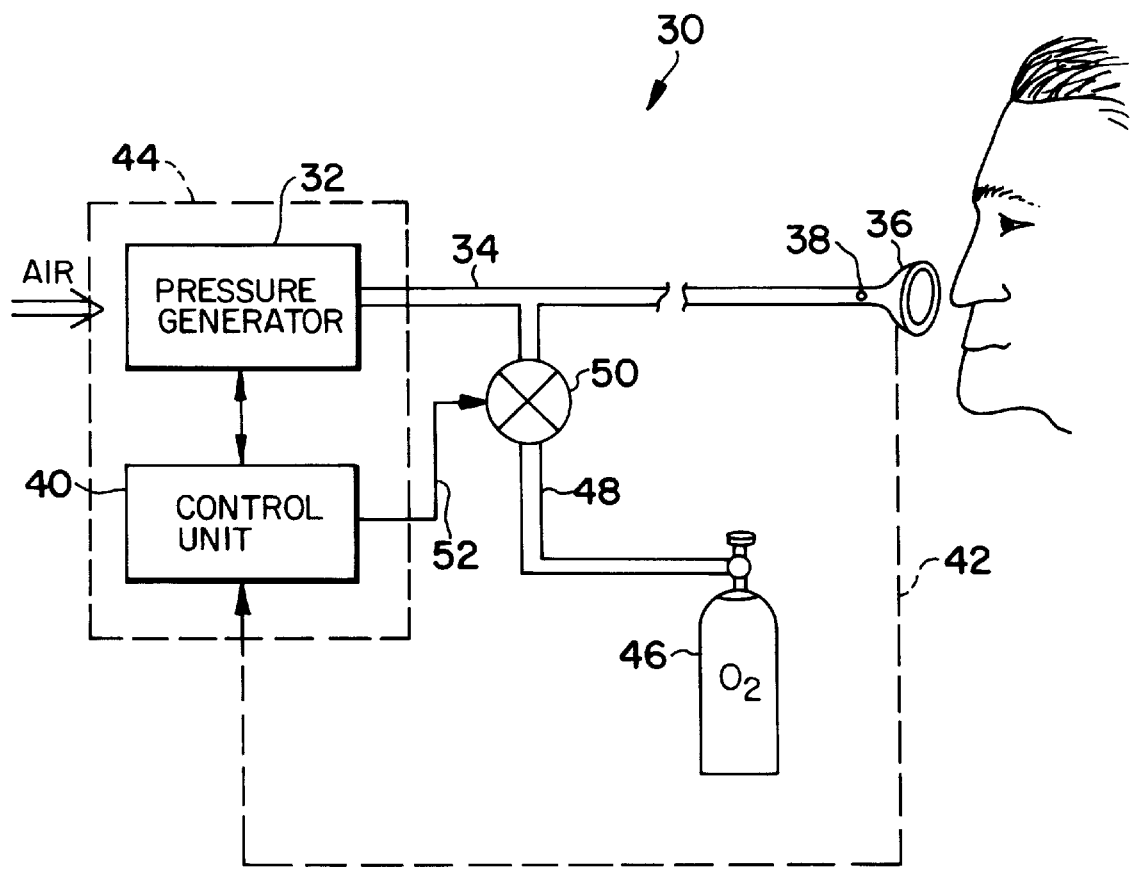
FIG. 1 is schematic diagram of a first embodiment of a pressure support system according to the principles of the present invention.

The basic components of a pressure support system 30 according to the principles of the present invention are discussed below with reference to FIG. 1. Pressure support system 30 includes a pressure generator 32 that receives a supply of breathing gas, such as air, via an inlet and delivers the breathing gas at an elevated pressure to a breathing circuit 34 as a primary flow of gas to be provided to a patient's airway. The present invention contemplates using any conventional pressure generating device, such as a piston-based or a blower-based device, for generating the primary flow of gas. It is to be understood that the source of breathing gas provided to pressure generator 32 can be sources other than air gathered from ambient atmosphere, such as gas from a pressurized tank.

In the illustrated embodiment, breathing circuit 34 is a conduit having one end coupled to the output of the pressure generator and another end coupled to a patient interface 36. Conduit 34 is any tubing suitable for carrying the primary gas flow to the patient. Typically, at least a portion of the breathing circuit 34 is flexible to allow for freedom of movement of the patient. It is to be understood that various components may be provided in or coupled to the breathing circuit. For example, a bacteria filter, pressure control valve, flow control valve, sensor, meter, pressure filter, humidifier, heater or any combination of these items can be provided in or attached to the breathing circuit.

Patient interface 36 is any device suitable for communicating the conduit with the airway of the patient, such as a nasal mask, oral mask or mouthpiece, nasal/oral mask, nasal cannula, trachea tube, intubation tube, hood or full face mask. It is to be understood that this list of suitable interface devices is not intended to be exclusive or exhaustive. Pressure generator 32, either alone or in combination with conduit 34 and patient interface 36, define the pressure generating system or pressure generating means of the present invention.

Typically, a majority of the exhaled gas from the patient exits the pressure generating system via an exhaust vent 38, which, in the illustrated embodiment, is provided on a portion of breathing circuit 34 near the patient interface. In some pressure generating systems, however, exhaled gas can vent to atmosphere through the pressure generator itself, by backing up through the inlet of the pressure generator, or through a pressure control valve associated with the pressure generator that vents a portion of the primary gas flow to atmosphere to control the pressure of that flow. Typically, exhaust vent 38 is merely an orifice provided in the breathing circuit that communicates the passageway in the conduit with atmosphere with no active control over the flow of gas from the system. It is to be understood, however, that a wide variety of exhaust devices and configurations are contemplated for use with the pressure generating system of the present invention.

A control unit 34 controls the operation of pressure generator 32. In its simplest form, control unit 40 merely actuates pressure generator 32, and, thus, may be nothing more than an on/off switch or similar input device. Such a switch may be provided on the same housing containing pressure generator 32 and/or may include a remote control unit to control actuation of the pressure generator from a remote location. In this relatively simple embodiment, pressure generator outputs a constant pressure and, thus, functions as a CPAP device.

In a more sophisticated embodiment, control unit 40 controls the operation of pressure generator 32 based on other variables, such as conditions of the pressure generating system (for example, the pressure detected in the breathing circuit), monitored conditions of the patient (for example, whether the patient is inhaling, exhaling, snoring or experiencing an apnea or hypopnea), and time based conditions (for example, increasing the pressure gradually over a period of time or breath cycles), to provide varying levels of pressure to the patient. The present invention contemplates varying the pressure level using any conventional technique, for example, using a separate pressure control valve or by controlling the speed of the blower or piston, all of which are considered as components of pressure generator 32 for purposes of the present invention.

An example of a pressure support system that provides a variable pressure to the patient based on patient's respiratory cycle it taught, for example, in U.S. Pat. Nos. 5,148,802 and 5,433,193 both to Sanders et al. and U.S. Pat. No. 5,313,937 to Zdrojkowski et al., the contents of which are incorporated by reference into the present application. In this embodiment in which the pressure output by the pressure generator varies based on the patient's respiratory cycle, sensors are provided that monitor the flow of gas in the conduit and the pressure at the conduit to determine the respiratory state of the patient. The control unit then varies the pressure of the primary gas flow depending on the respiratory state of the patient so that a higher pressure is provided to the patient during inhalation than during exhalation. Dashed line 42 in FIG. 1 illustrates the communication between a sensor at patient interface 36 to control unit 40. It is to be understood, however, that one or more sensors can be provided at other locations along the breathing circuit in place of or in addition to that illustrated in FIG. 1.

U.S. Pat. No. 5,492,113 to Estes et al., the contents of which are also incorporated by reference into the present application, teaches a variety of techniques for controlling the operation of a pressure support device, such a ramping the pressure of the primary gas flow, delaying providing the flow, resetting the following and/or automatically turning on or turning off the flow. Other patents, such as in U.S. Pat. No. 5,107,830 to Younes, the contents of which are incorporated herein by reference, disclose a proportional assist ventilation (PAV®) technique in which the pressure provided to the patient varies with patient effort. In addition, U.S. Pat. Nos. 5,535,738 and 5,794,615 both to Estes, the contents of which are incorporated herein by reference, discloses a proportional positive airway pressure (PPAP) ventilation technique in which the pressure provided to the patient varies with the flow of gas provided to the patient.

The combination of pressure generator 32 and the portions of control unit 40 associated therewith that control the operation of pressure generator 32 define a pressure support device 44. Any of the above-described conventional ventilation techniques, or any combination thereof, can be used in the pressure support device of the present invention. For example, pressure support device 44 may function as a conventional CPAP device, such as the Aria® LX device manufactured by Respironics. Inc. of Pittsburgh Pa, or may function as a conventional bi-level device that provides variable levels of pressure to the patient, such as the BiPAP® devices, also manufactured by Respironics. Inc. It is to be understood however, that pressure support device 44 can be other types of devices that perform other types of pressure support functions. For example, the present invention contemplates that the combination of pressure generator 32 and controller 40 can correspond to a pressure support device that provides proportional airway pressure ventilation or PAV, as taught, for example, in U.S. Pat. No. 5,044,362 to Younes, the contents of which are incorporated by reference into the present application, or that provides proportional positive airway pressure or PPAP, as taught, for example, in U.S. Pat. Nos. 5,535,738 and 5,794,615 both to Estes et al., the contents of which are already incorporated by reference into the present application, which teach providing PPAP to treat OSA and to treat congestive heart failure (CHF), respectively.

In addition to the pressure generating system that delivers a primary gas flow to the patient, the pressure support system of the present invention includes a supplemental gas system for providing a supplemental flow of gas to that patient. Typically, oxygen or an oxygen mixture, constitutes the supplemental gas. However, the present invention contemplates providing any type of gas or gaseous mixture, such as medicated gas, as the supplemental gas. The illustrated exemplary embodiment the supplemental gas system includes a source 46 of supplemental gas, a conduit 48 that delivers the supplemental flow of gas to the patient and a valve 50. It is to be understood that other components may be provided in the supplemental gas system. For example, a bacteria filter, pressure regulator/control valve, flow control valve, sensor, meter, pressure filter, humidifier, heater, or any combination of these items can be provided in or attached to conduit 48, gas source 46, or both. It is to be further understood that the source 46 of supplemental gas need not be a pressurized tank as shown. On the contrary, the present invention contemplates using any device that provides a source of supplemental gas as the gas source. An oxygen concentrator is an example of another suitable supplemental gas source.

Valve 50 operates under the control of control unit 40 to control the supplemental flow of gas to the patient. In this embodiment, control unit 40 in pressure generating device 44 communicates with valve 50 via a hardwired communication link 52 to control the operation of valve 50 based on conditions of pressure generator 32. More specifically, control unit 40 causes valve 50 to close to prevent the supplemental gas from entering pressure generator 32, its housing, or both. This may occur, for example, if pressure generator 32 ceases functioning, i.e., if the pressure generator is turned off or in the event of a power disruption or other malfunction, while the source of supplemental gas remains on. Supplemental gas can also enter pressure generator 32, its housing, or both if the pressure generator fails to generate a flow above a predetermined threshold. In which case, control unit 40 also causes valve 50 to close or to reduce the supplemental gas flow into conduit 34 so that the supplemental gas flow does not enter pressure generator 32.

By effectively shutting off or at least reducing the supply of supplemental gas in the event the pressure generator ceases operating at a required level of output pressure, the present invention prevents the supplemental gas, e.g., oxygen, from being introduced into the breathing circuit 34. This automatic shutoff or reduction function both conserves the supplemental gas and prevents it from entering the interior of pressure generator 32, as well as the housing in which the pressure generator is located, thereby minimizing the risk of fire due to the presence of concentrated oxygen in the mechanical/electrical pressure generator. Consequently, there is no build-up of supplemental gas in the local environment, such as the room in which pressure support system 30 is located, thereby minimizing the risk of fire due to ignition with external sources, such as a TV, heater or pilot light.

Valve 50 can have any configuration so long as it accomplished the gas shut-off function discussed above. However, in a preferred embodiment of the present invention, valve 50 is a normally closed two-position valve that is actuated responsive to a signal issued by the control unit so that it moves from the fully closed position to a fully open position as long as the control unit continues to provide the signal. This embodiment for valve 50 ensures that the valve will close to prevent oxygen flow from source 46 to breathing circuit 34 in the event of complete power loss or in the event communication link 52 is disrupted. It is to be understood that valve 50 can be configured to reduce the supplemental flow of gas as necessary instead of shutting off the supplemental flow entirely.

This reduction is the supplemental flow of gas can be accomplished, for example, by having the control unit operate the valve in a pulse modulation manner so as to output a train of pulses of supplemental gas. The duty ratio of the pulses and/or the period of the pulse train can be controlled to control the amount of supplemental gas delivered to the patient. This method of controlling the amount of supplemental gas delivered to the patient can also be used even if the pressure generator is functioning properly, for example, to control the dosage of supplemental gas delivered to the patient.

Figure 2:
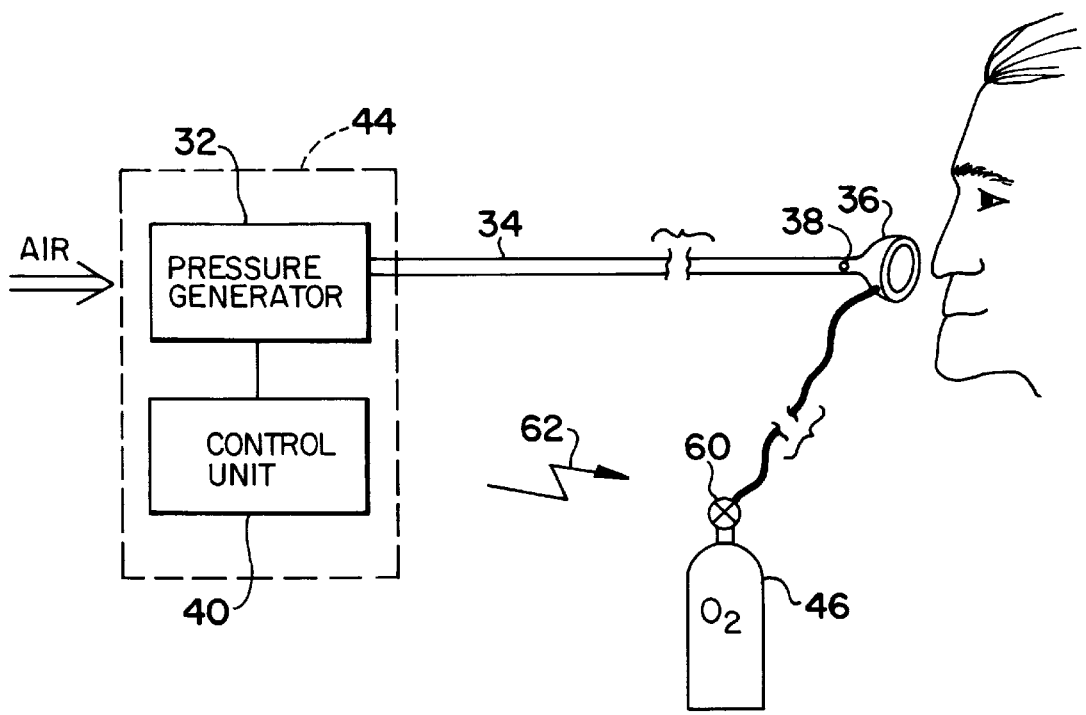
FIG. 2 is a schematic diagram of a second embodiment of a pressure support system according to the principles of the present invention.

The present invention further contemplates that valve 50 can be provided at any location along supplemental gas supply line 48 so long as it functions to block or reduce the supplemental flow of gas from source 46 to breathing circuit 34 and/or patient interface 36. For example, FIG. 2 illustrates an alternative embodiment of the present invention in which a valve 60 is provided on the outlet of a pressurized tank acting as the source of supplemental gas. In this embodiment, valve 60 communicates with control unit 40 via a wireless communication link 62, such as an rf or infrared signal.

Figure 3:
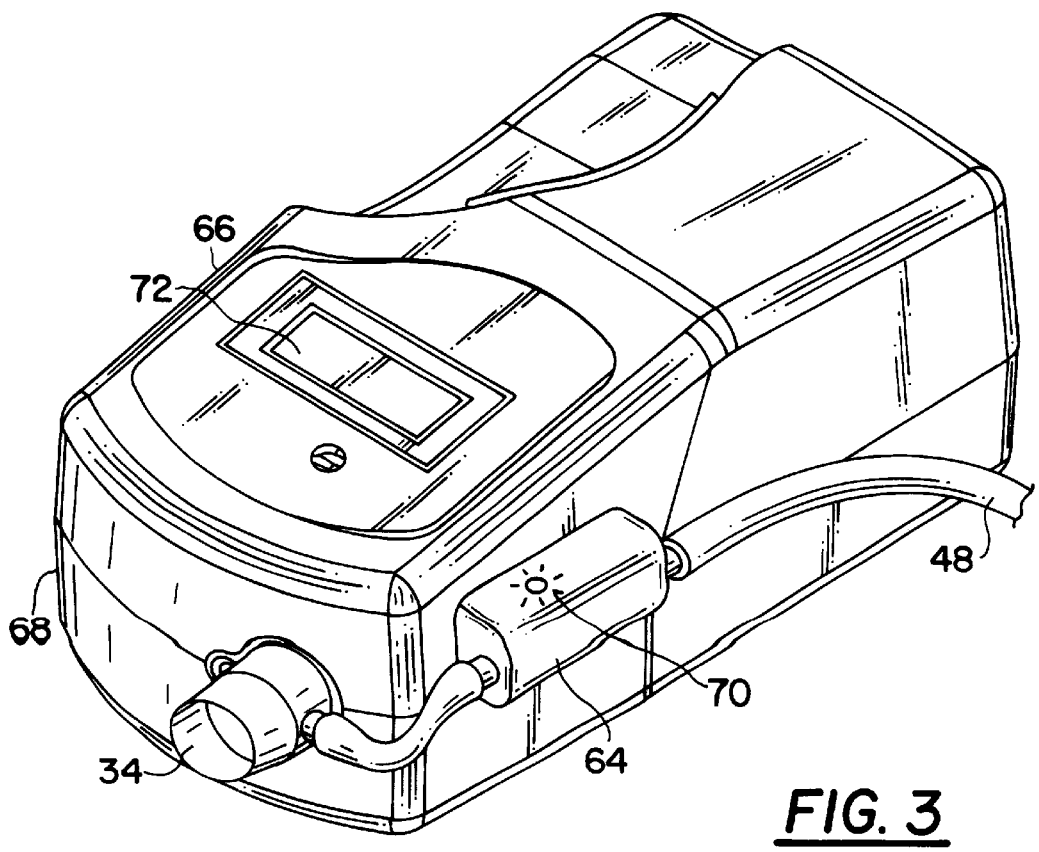
FIG. 3 is a perspective view of a pressure support device having a system for providing a supplemental flow of gas to a patient according to a third embodiment of the present invention.

FIG. 3 illustrates the supplemental flow control valve provided as an add-on module 64 to a conventional pressure support device 66, with the supplemental gas flow being introduced to breathing circuit 34 outside housing 68 for the pressure generator. It is to be understood, however, that the supplemental flow control valve can be provided within housing 68 and/or the supplemental flow of gas can be introduced into breathing circuit within the housing. In the embodiment illustrated in FIG. 3, the supplemental gas supply system includes an indicator 70 that informs the user when supplemental gas is flowing through tubing 48. Indicator 70 can be a visual indicator, an audio indicator, or both that enables the user to readily discern whether supplemental gas is flowing through module 64. For example, an LED can be lit when oxygen is flowing. Indicator 70 can be provided on module 64, as shown, or at other locations, such as on a display 72.

Although control unit 40 used to control valve 50 or 60 can be configured as a part the same control unit used to control the operation and/or the pressure or flow output by the pressure generator, it is to be understood that the control unit 40 can be a separate control system that monitors the operation of the pressure generator 32 and controls valve 50 or 60 as described above.

While the actuation of valve 50 has been discussed above as being controlled based on the operation of pressure generator 32, i.e., whether pressure generator 32 is operating or is outputting a flow above a predetermined threshold, it is to be understood that other embodiments of the present invention contemplating using control unit 50 to regulate valve 50 based on other conditions of the pressure support system. For example, a sensor can be provided to detect the level of supplemental gas in the pressure generator, its housing, or both, so that if this level exceeds a predetermined acceptable threshold, control unit 40 causes valve 50 to close or reduce the supplemental gas flow as discussed above. Similarly, a temperature sensor can be provided to detect the temperature of pressure generator 32, its housing, control unit 50, or any combination thereof, so that control unit 40 causes valve 50 to close or reduce the supplemental gas flow if the detected temperature exceeds a predetermined acceptable threshold.

In another embodiment of the present invention, in addition to being used as an automatic shutoff or flow reduction valve, valve 50 is used to control the supplemental flow of gas from source 46 into breathing circuit 34 based on the patient's breathing. More specifically, control unit 40 and valve 60 control the supplemental gas flow so that the supplemental gas flow is provided to the breathing circuit while the patient is breathing in (inspiring) and is not provided to the breathing circuit when the patient is breathing out (expiring). The techniques for triggering valve 50 to provide the supplemental flow in synchronization with the patient's breathing cycle are the same used to trigger the pressure generator to vary the pressure levels. See, for example, U.S. Pat. Nos. 5,148,802 and 5,433,193 to Sanders et al. discussed above.

In a still further embodiment, valve 50 is controlled to begin introducing the supplemental flow of gas into breathing circuit 34 just prior to inspiration, so that a sufficient supply of oxygen, for example, is available to the patient during the entire inspiratory phase. The oxygen is then shut off before or at the end of the inspiratory phase and remains shut of during a majority of the expiratory phase to conserve oxygen and prevent it from entering the pressure generator during patient expiration. The amount of time in which supplemental gas is provided to the patient during each respiratory cycle can be fixed to regulate the amount or dosage of supplemental gas delivered to the patient.

Furthermore, the supplemental gas flow system can be controlled as discussed above to control the dosage of supplemental gas delivered to the patient during each portion of the respiratory cycle that the supplemental gas is being delivered to the patient. It may be particularly advantageous to control the dosage of supplemental gas in this manner in situations where the supplemental gas contains a medication.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A pressure support system comprising:
    (1) a pressure generating system adapted to provide a primary flow of gas to a patient, the pressure generating system comprising:
        (a) an electrically powered pressure generator adapted to receive a supply of breathing gas from a breathing gas source and to produce the primary flow of gas responsive to power being provided to the pressure generator, and
        (b) a control unit operatively coupled to the pressure generator for controlling a supply of electrical power to the pressure generator so as to cause the pressure generator to output the primary flow of gas;

(2) a supplemental gas system adapted to provide a supplemental flow of gas to such a patient in conjunction with the primary flow of gas; and (3) a selectively actuatable valve associated with the supplemental gas system and with the control unit, wherein the valve substantially disables the supplemental flow of gas responsive to the control unit disabling the supply of electrical power to the pressure generator.

2. A pressure support system according to claim 1, wherein the valve is a normally closed valve that is actuated to cause it to move to an open position responsive to a signal from the control unit, and wherein the signal is output by the control unit responsive to a determination that the pressure generator is at least one of (1) actuated and (2) operating within normal parameters.

3. A pressure support system according to claim 1, further comprising a monitoring system operatively coupled to the supplemental gas system, wherein the monitoring system monitors the supplemental flow of gas in the supplemental gas system and provides an output indicative of whether gas is flowing in the supplemental gas system.

4. A pressure support system according to claim 1, wherein the pressure generating system further monitors a respiratory cycle of a patient, and wherein the control unit causes the supplemental gas system to deliver the supplemental flow of gas to a patient during a selected portion of a respiratory cycle by causing the valve to open at an appropriate time to deliver the supplemental flow of gas during the selected portion of a respiratory cycle and to close at all other times during the respiratory cycle.

5. A pressure support system according to claim 4, wherein the pressure generating system varies a pressure of the primary flow of gas delivered to a patient based on patient respiration.

6. A pressure support system according to claim 4, wherein the control unit causes the valve to open according to a predetermined duty ratio to control an amount of supplemental gas delivered to a patient during the selected portion of a respiratory cycle.

7. A pressure support system according to claim 1, wherein the control unit causes the valve to open according to a predetermined duty ratio to control an amount of supplemental gas delivered to a patient.

8. A pressure support system according to claim 1, wherein
(1) the pressure generating system includes a first conduit operatively coupled to the pressure generator to deliver the primary flow of gas from the pressure generator to a patient,
(2) the supplemental gas system includes:
a source of gas, and
a second conduit operatively coupled to the source of gas and to the first conduit, and
(3) the valve is operatively coupled to the second conduit to control the supplemental flow of gas from the second conduit to the first conduit.

9. A pressure support system according to claim 8, wherein the pressure generating system includes means for varying a pressure of the primary flow of gas.

10. A pressure support system according to claim 8, wherein the valve is remote from the control unit and communicates with the control unit via a wireless transmission.

11. A pressure support system according to claim 8, wherein the valve is a normally closed valve that is actuated to cause it to move to an open position to allow the supplemental flow of gas to a patient responsive to a signal from the control unit, and wherein the signal is output by the control unit responsive to a determination that the pressure generating system is at least one of (1) actuated and (2) operating within normal parameters.

12. A pressure support system comprising:
pressure generating means, including an electrically powered pressure generator, for providing a primary flow of gas to a patient responsive to power being provided to the pressure generator;
controlling means for controlling a supply of electrical power to the pressure generator so as to cause the pressure generator to output the primary flow of gas;
supplemental gas means for providing a supplemental flow of gas to such a patient in conjunction with the primary flow of gas;
flow controlling means, associated with the pressure generating means and the supplemental gas means, for controlling the supplemental flow of gas delivered to a patient by the supplemental gas means, wherein the flow controlling means substantially disables the supplemental flow of gas responsive to the controlling means disabling the supply of electrical power to the pressure generating means.

13. A pressure support system according to claim 12, wherein the flow controlling means monitors operation of the pressure generator and substantially disables the supplemental flow of gas to the patient via the supplemental gas means responsive to a determination by the flow controlling means that the pressure generator is at least one of (1) inoperative and (2) not generating a flow above a predetermined threshold.

14. A pressure support system according to claim 12, further comprising monitoring means for monitoring a supplemental flow of gas provided by the supplemental gas means and for providing an output indicative of the supplemental flow of gas.

15. A pressure support system according to claim 12, wherein the pressure generating means monitors a respiratory cycle of a patient, and wherein the flow controlling means causes the supplemental flow of gas to be delivered to a patient only during a selected portion of the respiratory cycle.

16. A pressure support system according to claim 15, wherein the flow controlling means includes means for controlling a dosage of supplemental gas delivered to a patient during the selected portion of the respiratory cycle.

17. A pressure support system according to claim 12, wherein the pressure generating means monitors a respiratory cycle of a patient and varies a pressure of the primary flow of gas delivered to a patient based on the respiratory cycle.

18. A pressure support system according to claim 12, wherein
(1) the pressure generating means includes a first conduit operatively coupled to the pressure generator to deliver the primary flow of gas from the pressure generator to a patient;
(2) the supplemental gas means includes:
a source of gas,
a second conduit operatively coupled to the source of gas and to the first conduit; and
(3) the flow controlling means includes a valve operatively coupled to the second conduit to control the supplemental flow of gas from the second conduit to the first conduit.

19. A pressure support system according to claim 18, wherein the flow controlling means includes processing means for controlling operation of the pressure generating means and for controlling actuation of the valve based on monitored conditions of the pressure generator.

20. A pressure support system according to claim 19, wherein the valve is a normally closed valve that is actuated to cause it to move to an open position responsive to a signal from the processing means, and wherein the signal is output by the processing means responsive to a determination that the pressure generator is at least one of (1) actuated and (2) operating within normal parameters.

21. A method of providing pressure support to a patient comprising the steps of:
   providing a primary flow of gas to a patient via a first flow system that includes an electrically powered pressure generator responsive to power being provided to the pressure generator;
   controlling a supply of electrical power to the pressure generator so as to cause the pressure generator to output the primary flow of gas;
   providing a supplemental flow of gas to a patient via a second flow system in conjunction with the primary flow of gas;
   controlling the supplemental flow of gas delivered to a patient so as to substantially disable the supplemental flow of gas responsive to the supply of electrical power to the pressure generating means being discontinued.

22. A method of providing pressure support, according to claim 21, further comprising a step of monitoring a respiratory cycle of the patient, and wherein the step of controlling the supplemental flow of gas includes providing the supplemental flow of gas only during a selected portion of the respiratory cycle.

23. A method of providing pressure support, according to claim 22, further comprising:
   controlling a dosage of a supplemental gas delivered to a patient as the supplemental flow of gas during the selected portion of the respiratory cycle.

24. A method of providing pressure support, according to claim 21, further comprising:
   monitoring the supplemental flow of gas to provided by the second flow system; and
   outputting a signal indicative of whether the supplemental flow of gas is present.

* * * * *